United States Patent [19]

Leach

[11] 4,283,574
[45] Aug. 11, 1981

[54] PROCESS FOR THE SYNTHESIS OF 2,6-XYLENOL AND 2,3,6-TRIMETHYLPHENOL

[75] Inventor: Bruce E. Leach, Ponca City, Okla.

[73] Assignee: Conoco, Inc., Ponca City, Okla.

[21] Appl. No.: 116,061

[22] Filed: Jan. 28, 1980

[51] Int. Cl.³ .............................................. C07C 37/11
[52] U.S. Cl. ...................................... 568/804; 568/794
[58] Field of Search .................................. 568/794, 804

[56] References Cited

U.S. PATENT DOCUMENTS

| | | | |
|---|---|---|---|
| 3,290,389 | 12/1966 | Hahn | 568/731 |
| 3,446,856 | 5/1969 | Hamilton | 568/804 |
| 3,479,410 | 11/1969 | Hamilton | 568/804 |
| 3,491,163 | 1/1970 | Kenton | 568/804 |
| 3,542,750 | 11/1970 | Tomomaysu | 568/794 |
| 3,670,030 | 6/1972 | Sparks | 568/794 |
| 3,737,466 | 6/1973 | Sharp | 568/804 |
| 3,994,982 | 11/1978 | Leach | 568/804 |
| 4,100,207 | 7/1978 | Goodwin | 568/804 |
| 4,110,253 | 8/1978 | Leach | 568/804 |
| 4,126,750 | 11/1978 | Poe | 568/804 |
| 4,201,880 | 5/1980 | van Sorge | 568/804 |
| 4,208,537 | 6/1980 | Kawamata | 568/804 |

FOREIGN PATENT DOCUMENTS

| | | | |
|---|---|---|---|
| 1102309 | 2/1968 | United Kingdom | 568/804 |
| 1228174 | 4/1971 | United Kingdom | 568/804 |

*Primary Examiner*—Werren B. Lone
*Attorney, Agent, or Firm*—Cortlan R. Schupbach, Jr.

[57] ABSTRACT

Phenol is methylated over an alumina catalyst using methanol, and the reaction product therefrom is combined with additional methanol over a promoted magnesium oxide catalyst. Major reaction products are ortho-cresol, 2,6-xylenol and 2,3,6-trimethylphenol. The promoted magnesium oxide catalyst contains metal promoters selected from the group consisting of titanium, chromium, and uranium together with sulfate ions.

11 Claims, No Drawings

PROCESS FOR THE SYNTHESIS OF 2,6-XYLENOL AND 2,3,6-TRIMETHYLPHENOL

This invention relates to the methylation of phenol. More specifically, this invention relates to a two-step methylation of phenol to produce predominantly orthocresol, 2,6-xylenol and 2,3,6-trimethylphenol.

2,6-xylenol is useful as a precursor to 2,3,6-trimethylphenol and other useful products. 2,6-xylenol also finds uses in polymer and plastics applications such as those described in U.S. Pat. No. 3,446,856. 2,3,6-trimethylphenol is useful as an intermediate in Vitamin E synthesis. Ortho-Cresol is useful in chemical applications as an intermediate, for example, as a precursor to 6-chloro-2-methylphenol which is used in the synthesis of herbicides. Other uses are well known to those skilled in the art.

Many aluminum oxide catalysts (aluminas) are known in the art. Of these, gamma aluminas are preferred for many reactions involving phenols, whether carried out in either the vapor or liquid phase. These reactions are carried out by reacting phenol and olefins or alcohols to introduce hydrocarbon groups onto the aromatic ring of a phenol. Representative examples of such processes are U.S. Pat. Nos. 3,290,389, 3,369,981, 3,542,750, 2,450,766, 3,670,030, and British Patent No. 1,102,309. These processes together or singly teach reacting phenols with olefins in the presence of a gamma alumina for purposes such as polymerizing cyclic alkylene oxides, introducing hydrocarbon groups onto rings of a phenol, and production of phenols alkylated in the ortho position.

In addition, a long catalyst life, high activity liquid phase process is shown in U.S. Pat. No. 3,994,982, hereby incorporated in its entirety into the instant specification by reference.

Vapor phase methylation of phenols over magnesium oxide is taught in U.S. Pat. No. 3,479,410 which also requires the presence of 2,4,6-trimethylphenol as an ingredient in the feestream. Catalysts containing magnesium oxide and tungsten oxide are known for the disproportionation of olefins such as taught in U.S. Pat. No. 3,491,163. U.S. Pat. No. 4,110,253 shows the method of promoting magnesium oxide with tungsten oxides to provide a long-lived easily regenerable catalyst suitable for the disproportionation of highly alkylated phenols with phenol. These catalysts likewise have excellent crush resistance.

However, purification of the major products of these and similar reactions has been a problem. This is especially true when 2,6-xylenol is produced along with meta- and para-cresols (m,p-cresols). Due to the great similarity in the boiling points in these compounds, it would be greatly desirable to have direct methylation of phenol under conditions which minimize formation of undesirable by-products while forming desirable products such as orthocresol, 2,6-xylenol, and 2,3,6-trimethylphenol.

It is therefore an object of the present invention to provide an improved, two-step process for the direct methylation of phenol to produce 2,6-xylenol, orthocresol and 2,3,6-trimethylphenol in high proportion. Other objects will become apparent to those skilled in this art as the description proceeds.

In accordance with the present invention, we have discovered an improved process for selectively producing 2,6-xylenol, 2,3,6-trimethylphenol, and orthocresol in high proportions by carrying out a direct methylation of phenol in the presence of a gamma alumina, then using the product stream from this reaction as a direct feed to a second step, which directly methylates the feedstream with additional methanol in the presence of a magnesium oxide catalyst promoted with amorphous metal ions of titanium, uranium, and chromium together with sulfate ions. This process is an improvement over the heretofore known processes in many regards, giving exceptionally high proportions of desired products. The linking of two distinct alkylation processes without any separation of the feedstream of the first process before carrying out the second alkylation in the presence of a promoted magnesium oxide catalyst allows for extremely high conversion of phenol during a single pass of the two-stage process.

In the first stage of the process, phenol can be alkylated using any of the prior art processes involving gamma alumina catalysts, both liquid and vapor phase. For most purposes, a vapor phase process will be employed, since it is easier to reduce pressure to the pressure of the second step of the process, as opposed to a high-pressure liquid phase process. The advantages of selectivity of the liquid phase process are desirable, but are not necessary in the process of the instant invention, since an excellent conversion to the three desired main components is obtained.

Normally, in carrying out the first step in the process of the present invention from about 0.2 mole to about 1.0 mole of methanol or any other suitable methylating agents such as iso-butylene are used per mole of phenol, but from about 0.4 mole to about 0.8 mole is preferred. Methanol is preferred as a methylating agent. Temperatures of from 300° C. to 400° C. are preferred for this reaction. In continuous reactions, liquid hourly space velocities (LHSV) of from about 1 to 10 can be used and from about 2 to 8 are preferred. The pressures used will depend on whether the process is being carried out in liquid or vapor phase, but normally pressures of from about atmospheric to about 1000 per square inch gauge are preferred.

In the second stage of the instant invention, the products stream from the first stage containing a mixture of alkylated phenols and additional alkylating agent is passed directly into contact with the promoted magnesium oxide catalysts at a new mole ratio of from about 1 to about 10, a temperature ranging from about 400° to about 500° C. and a pressure ranging from about atmospheric to about 5 atmospheres. When carried out continuously, an LHSV of from about 1.0 to about 10.0 is used.

The magnesium oxide catalyst of the second stage is promoted with from about 2 to about 10 weight percent sulfate ion and from about 2 to about 10 weight percent metal ions selected from the group consisting of amorphous titanium, chromium, and uranium. For crush strength and additional surface area, optionally from 1 to 5 weight percent silica can be used, and from 1 to 3 weight percent graphite can be inserted as a lubricant. While silica tends to further promote the catalyst, its primary purpose is for crush resistance and surface area of the catalyst pellets.

The process of the present invention can be carried out efficiently in either batch or continuous flow reactors. Of these, the continuous flow reactors are preferred. Flow from the first stage to the second stage can be carried out quite easily. In the continuous flow reactor scheme, the alumina catalyst and the magnesium oxide catalysts are both suitably divided and placed in position to catalyze the reaction between the phenol and the methylating agent in the first stage, and the product stream from the first reaction and additional methylating agent in the second stage. Reactor flow in both cases can be either upward or by gravity; however, gravity flow is preferred.

The two-stage process of the present invention greatly reduces unwanted by-products in the reaction. In a reaction carried out using both stages, ortho-cresol can be obtained in amounts ranging from 5-40 percent, 2,6-xylenol in amounts of 10-40 percent, and 2,3,6-trimethylphenol in amounts of 10-40 percent. Most other by-products, with the exception of 2,4,6-trimethylphenol, are present in substantially less than 1 percent amount. By-products which are especially undesirable, such as meta- paracresol, likewise fall below 1 percent of the final product, thus being produced in a lower by-products/product ratio.

The invention is more completely described with reference to the examples below wherein all parts and percentages are by weight unless otherwise specified. The examples are provided to illustrate the instant invention and not to limit it.

The data disclosed herein was generated using a ½-inch stainless steel reactor containing 1/16-inch catalyst pellets. Flow in the reactor could be varied either upward or by gravity.

EXAMPLE 1

A sample was collected from a commercial operating plant using phenol methylated with methanol. The reaction was a vapor phase reaction carried out with a temperature of from about 370° to about 420° C., a pressure from ATM to 3 ATM, an LHSV of about 3.5, a methanol-to-phenol mole ratio of about 0.7.

A sample of the product stream from this reaction was obtained and analyzed prior to being inserted through the second magnesium oxide reaction. The composition of this product stream (feed to the second stage) is set forth in Table 1.

EXAMPLE 2

A ½-inch diameter stainless steel reactor was loaded with 20 cubic centimeters (cc) of catalyst. Catalyst was prepared by adding 6 grams of titanium isopropoxide to 90 grams of magnesium oxide (MERCK MAGLITE-D, trademark of and sold by Merck Chemical Company) followed by the addition of 2 grams of ammonium sulfate in aqueous solution and 10 grams of 30 percent colloidial silica in water. The mixture was air-dried and tableted. The tablets were dried at 150° C. for 2 hours, then calcined in air at 500° C. for two hours.

The feed mixture was passed over the catalyst at a reaction temperature of about 460° C. Reaction was carried out continuously using a liquid hourly space velocity of 3.0. The methanol mole ratio was 100 parts feed material to 137.5 parts of methanol by weight. The results are set forth in Table 1 below.

TABLE 1

| Component | Example 1 Product | Example 2 Product |
|---|---|---|
| Methanol loss | | 3.38 |
| Methanol | 52.33 | 32.38 |
| Water | 9.10 | 15.81 |
| Anisole | 0.40 | 0.39 |
| Phenol | 22.68 | 0.98 |
| o-Methylanisole | Tr | 0.13 |
| o-Cresol | 9.74 | 11.39 |
| m,p-Cresol | 0.26 | 0.07 |
| 2,6-Dimethylanisole | Tr | 0.07 |
| 2,6-Xylenol | 2.43 | 28.39 |
| 2,4-/2,5-Xylenol | 0.64 | 0.97 |
| 2,3-Xylenol | 0.39 | 0.20 |
| 2,4,6-Trimethylanisole | Tr | 0.10 |
| 2,4,6-Trimethylphenol | 0.63 | 2.99 |
| 2,3,6-Trimethylphenol | 0.96 | 2.04 |
| 2,3,5-/2,4,5-Trimethylphenol | 0.09 | 0.11 |
| 2,3,4-/3,4,5-Trimethylphenol | 0.08 | 0.07 |
| Pentamethylbenzene | Tr | Tr |
| 2,3,4,6-/2,3,5,6-Tetramethylphenol | 0.15 | 0.41 |
| 2,3,4,5-Tetramethylphenol | Tr | Tr |
| Hexamethylbenzene | Tr | Tr |
| Pentamethylphenol | 0.05 | 0.12 |

A materials balance was made and the results are set forth in Table 1. Phenol conversion was 97 percent total for both steps and selectivity to ortho-cresol, 2,6-xylenol and 2,3,6-trimethylphenol was 89 percent for the combined reaction sequence. Methanol usage was much more selective than for typical magnesium oxide catalysts. Selectivity based on methanol was 93 percent, compared to a typical value of 70 percent for prior art magnesium oxide reactions without a prior alkylation over alumina. Major advantages appear to be obtained because the meta-containing substitution products of the alumina-catalyzed reaction are coupled with the high per pass phenol conversion over the magnesium oxide catalysts of the present invention which have high ortho substituion selectivity.

EXAMPLE 3

The procedure set forth in Examples 1 and 2 was repeated, and a reaction was carried out for 24 hours. Methanol loss was determined by the weight of feed/weight of product in the run. Methanol recovery was made by distillation. Water was also determined by distillation followed by extraction with $CH_2Cl_2$ to remove phenolics. The phenolics removed were analyzed by gas chromatography. Table 1 shows the combined analysis of all fractions isolated.

EXAMPLE 4

A silica-free catalyst was prepared by adding 15 grams of titanium isopropoxide to 180 grams of magnesium oxide (Merck Maglite D), followed by the addition of 6.25 g of magnesium sulfate and 4 g of graphite. The mixture was tableted and calcined as described in Example 2. A reaction was carried out using the same feed described in Example 1. The reaction was carried out at a temperature of 468° C., pressure of 40 psig and LHSV of 1.4 and 3.0. The catalyst had a lower crush strength than silica-containing catalysts and was slightly less active. The results are set forth in Table 2. Example 2 product column is on a 100 percent phenolics basis, without water and methanol and is equivalent to the Example 2 product column in Table 1.

TABLE 2

| Component | Example 2 Product | 3.0 LHSV | 1.4 LHSV |
|---|---|---|---|
| Anisole | 0.81 | 1.42 | 1.30 |
| Phenol | 2.02 | 10.02 | 0.96 |
| o-Methylanisole | 0.27 | 0.45 | 0.77 |
| o-Cresol | 23.52 | 35.68 | 17.01 |
| m,p-Cresol, 2,6-Dimethyl- | | | |

TABLE 2-continued

| Component | Example 2 Product | 3.0 LHSV | 1.4 LHSV |
|---|---|---|---|
| anisole | 0.28 | 0.66 | 0.66 |
| 2,6-Xylenol | 58.62 | 36.29 | 60.31 |
| 2,4-/2,5-Xylenol | 2.00 | 4.10 | 2.48 |
| 2,3-Xylenol | 0.41 | 0.64 | 0.28 |
| 2,4,6-Trimethylanisole | 0.21 | Tr | 0.16 |
| 2,4,6-Trimethylphenol | 6.17 | 6.12 | 10.83 |
| 2,3,6-Trimethylphenol | 4.21 | 3.22 | 3.76 |
| Other Trimethylphenols | 0.37 | 0.47 | 0.37 |
| Pentamethylbenzene | Tr | Tr | Tr |
| Tetramethylphenols | 0.85 | 0.75 | 0.91 |
| Pentamethylphenol | 0.25 | 0.18 | 0.20 |

Thus, it can be seen that the present invention gives extremely high selectivity to the desired products without increasing the severity of reaction conditions and without increasing amounts of by-products, especially undesirable by-products such as meta-para-cresol. It is readily apparent that this improved two-step process is much superior to those provided in the prior art as single-step processes.

While certain embodiments and details have been shown for the purpose of illustrating this invention, it will be apparent to those skilled in this art that various changes and modifications may be made herein without departing from the spirit or scope of the invention.

We claim:

1. An improved method for the direct methylation of phenol to produce predominately ortho-cresol, 2,6-xylenol, and 2,3,6-trimethylphenol, wherein phenol is methylated over alumina catalyst to produce a product stream, the improvement comprising passing the product stream through a second methylation over a catalyst in the presence of from about 1 to about 10 mole ratio of methanol at a temperature of from 400° C. to about 500° C., and a pressure of from about atmospheric to about 5 atmospheres, wherein the catalyst is magnesium oxide promoted with amorphous metal ions selected from the group consisting of titanium, uranium, and chromium and sulfate ions.

2. A method as described in claim 1 wherein the metal ions are titanium ions.

3. A method as described in claim 1 wherein the process is carried out continuously.

4. A method as described in claim 1 wherein the catalyst contains from about 2 to 10 weight percent metal, and from about 2 to 10 weight percent sulfate ions.

5. A method as described in claim 4 wherein in addition, the catalyst contains from 1 to 5 weight percent silica.

6. A method as described in claim 5 wherein the catalyst contains from 1 to 3 weight percent graphite as lubricant.

7. A method as described in claim 5 wherein the process is carried out continuously.

8. A method as described in claim 7 wherein the liquid hourly space velocity is from about 1 to about 10.

9. A method as described in claim 8 wherein the reaction is carried out at a temperature of from about 440° to about 480° C., a pressure of from about atmospheric to about 2 atmospheres, mole ratio of methanol to first stage reactant product of from about 1.0 to 5 and wherein the liquid hourly space velocity is from about 1.0 to 5.

10. A method as described in claim 7 wherein the first stage methylation is carried out in the vapor phase.

11. A method as described in claim 7 wherein the first stage methylation is carried out in liquid phase.

* * * * *